United States Patent [19]

Gehrke

[11] Patent Number: 4,820,639

[45] Date of Patent: Apr. 11, 1989

[54] PROCESS FOR ENHANCING TRANSLATIONAL EFFICIENCY OF EUKARYOTIC MRNA

[75] Inventor: Lee Gehrke, Framingham, Mass.

[73] Assignee: Massachusetts Institute of Technology, Cambridge, Mass.

[21] Appl. No.: 804,672

[22] Filed: Dec. 4, 1985

[51] Int. Cl.$^4$ .................. C12P 21/00; C12P 19/34; C12N 15/00

[52] U.S. Cl. ........................ 435/68; 435/70; 435/91; 435/172.3; 435/317.1; 435/320; 935/30; 935/32; 935/34; 935/41; 935/57

[58] Field of Search ............ 415/68, 70, 91, 253, 415/320, 317.1; 935/317, 240, 30, 32, 34, 41, 57, 67, 70

[56] References Cited

PUBLICATIONS

Guilley et al., (1978), Cell, vol. 15, pp. 113–122.
Pyne et al., (1979), Intervirology, vol. 11, pp. 22–29.
Pelletier et al., (1985), Cell vol. 40, pp. 515–526.
Gehrke et al., (1983), Biochemistry, vol. 22, pp. 5157–5164.
Kozak, (1984), Nature, vol. 308, pp. 541–546.
Ameloof et al., (1985) J. Mdded. Fac. Landbouwwet, vol. 50, pp. 1281–1282 (abstr.).
Herson et al., (1979) J. Biol. Chem. 254: 8245–8249.
P. Ameloot et al., Med. Fac. Landbouww. Rijksuniv. Gent, 50/3b, 1281–1282 (1985).
D. R. Gallie, et al., Nucleic Acids Research, 15 (8), 3257–3273, (1987).
S. A. Jobling & Lee Gehrke, Nature, 325 (105), 622–625 (1987).
Gallie, et al., Nucleic Acids Research, (15(21), 8693–8711 (1987).
Gallie, et al., Nucleic Acids Research, 16(3), 883–893 (1988).
Sleat et al., Gene, 217, 217–225 (1987).
Jobling et al., Nature, 325(6105), 622–625 (Feb. 12, 1987).
Translational Control of Protein Synthesis, by Harvey Lodish in Ann. Rev Biochem, 45:39–72 (1976).
Competition between Globin Messenger Ribonucleic Acids for a Discriminating Initiation Factor by Kabat and Chappell in J. Biol. Chem., 252(8): 2684–2690, (1977).
Translational Control of Protein Synthesis During the Early Stages of Differentiation of the Slime Mold Dictyostelium Discoideum by Cell, 12:301–310 (1977).
Disproportionate Expression of the Two Nonallelic Rat Insulin Genes in a Pancreatic Tumor is Due to Translational Control by Barbara Cordell, et al, in Cell, 31:531–542 (1982).
Differential Translation of Mouse Myeloma Messenger RNA's in a Wheat Germ-Free System by G. E. sonenshein et al, in Biochem., 15:5501–5506 (1976).
Role of mRNA Competition in Regulating Translation: Further Characterization of mRNA Discriminatory Initiation Factors by B. K. Ray, et al., in Proc. Natl. Acad. Sci., USA, 80:663–667 (1983).

(List continued on next page.)

*Primary Examiner*—Thomas G. Wiseman
*Assistant Examiner*—S. Seidman
*Attorney, Agent, or Firm*—Kilpatrick & Cody

[57] ABSTRACT

A process and means for increasing the production of protein translated from eukaryotic messenger ribonucleic acid (mRNA) comprising transferring a regulatory nucleotide sequence from a viral coat protein mRNA to the 5' terminus of a gene or complementary deoxyribonucleic acid (cDNA) encoding the protein to be produced to form a chimeric DNA sequence. The regulatory DNA sequence are generated de novo using genetic engineering procedures to produce synthetic double-stranded oligonucleotides representing the regulatory viral sequence. Nucleotide sequences which encode a regulatory sequence or structure conferring enhanced competitive activity and increased rate of translation upon the chimeric DNA sequences include the nucleotide sequence preceding the initiator AUG codon at the 5' terminus of coat protein messenger RNA from alfalfa mosaic virus, brome mosaic virus, black beetle virus, turnip yellow mosaic virus, and satellite tobacco necrosis virus.

19 Claims, 5 Drawing Sheets

PUBLICATIONS

Competitive mRNA Translation in an in Vitro System from Wheat Germ, by D. Herson et al, in J. Biol. Chem., 254(17):8245–8249 (1979).

Structure of the 5'-Terminal Untranslated Region of the Genomic RNAs from Two Strains of Alfalfa Mosaic Virus, by M. Ravelonandro et al, in Nucleic Acids Research, 11(9), 2815–2826 (1983).

Comparison of Three Different Cell-Free Systems for Turnip Yellow Mosaic Virus RNA Translation, by W. Zagorski et al., in Biochimie, 65:127–133 (1983).

Translational discrimination between the Four RNAs of Alfalfa Mosaic Virus, by T. Godefroy-Colburn et al, in *Eur. J. Biochem.*, 147:541–548 ( 1985).

Cap Accessibility Correlates with the Initlation Efficiency of Alfalfa Mosaic Virus RNAs, by T. Godefroy-Colburn et al, in *Eur. J. Biochem.*, 147:549–552 (1985).

Differential Translation of Turnip Yellow Mosaic Virus mRNAs in Vitro, by C. Benicourt et al, in Biochem. Biophy. Res. Commun., 84(4):831–839 (1978).

Translational Regulation of Expression of the Brome-Mosiac-Virus RNA Genome In Vitro, by W. Zagorski in *Eur. J. Biochem.*, 86:465–472 (1978).

Early and Late Functions in a Bipartite RNA Virus: Evidence for Translational Control by Competition Between Viral mRNA's, P. D. Friesen et al, in J. Virol., 49(1):116–124 (1984).

Efficient Ribosome Binding of Brome Mosaic Virus (BMV) RNA4 Contributes to its Ability to Outcompete the other BMV RNAs for Translation, by J. W. Pyne et al, in Intervirology, 11:23–29 (1979).

5'-Conformation of Capped Alfalfa Mosaic Virus Ribonucleic Acid 4 May Reflect its Independence of the Cap Structure or of Cap-Bindng Protein for Efficient Translation, by Lee Gehrke et al, in Biochem., 22:5157–5164 (1984).

Characterization of Eukaryotic Initiation Factor 4A, A Protein Involved in ATP-Dependent Binding of Globin mRNA, by J. A. Grifo et al, in J. Biol. Chem., 257(9):5246–5252 (1982).

Secondary Structure of mRNA and Efficiency of Translation Initiation, by D. Iserentant et al, in Gene, 9:1–12 (1980).

Evaluation of the Scanning Model for Initiation of Protein Synthesis in Eucaryotes, by M. Kozak in Cell, 22:7–8 (1980).

Possible Role of Flanking Nucleotides in Recognition of the AUG Initiator Codon, by Eukaryotic Ribosomes in Nucleic Acids Research, 9(20):5233–5252 (1981).

Translation of Insulin-Related Polypeptides from Messenger RNAs with Tademly Reiterated Cpies of the Ribosome Binding Site, by M. Kozak in Cell, 34:971–978 (1983).

Eukaryotic Ribosomes can Recognize Preproinsulin Initiation Condons Irrespective of their Position Relative to the 5' End of mRNA, by Lomedico and McAndrew in Nature, 299:221–226 (1982).

Effect of a Purified Initiation Factor F3(B) on the Selection of Ribosomal Binding Sites on Phage MS2 RNA, by Berissi et al, in Nature New Biology, 234:44–47 (1971).

Probing the Function of the Eucaryotic 5' Cap Structure by Using a Monoclonal Antibody Directed against Cap-Binding Proteins, by Somenberg et al, in Cell, 27:563–572 (1981).

Initiation Factor-Dependent Binding of MS2 RNA to 30-S Ribosomes and the Recycling of IF-3 by Vermeer et al in Eur. J. Biochem, 40:295–308 (1973).

Complete Nucleotide Sequence of Alfalfa Mosaic Virus RNA 4, by Brederofe et al, in Nucleic Acids Research, 8(10):2213–2223 (1980).

Primary and Secondary Structure of Balck Beetle Virus RNA2, the Genomic Messenger for BBV Coat Protein Precursor, by Dasgupta et al, in Nucleic Acids Research, 12(19):7215–7223 (1984).

Sequence of the 3' Untranslated Region of Brome Mosaic Virus Coat Protein Messenger RNA, by Dasgupta et al, in Birology 104:339–346 (1980).

Total Nucleotide Sequence of a Nearly Fullsize DNA Copy of Satellite Tobacco Necrosis Virus RNA, by Ysebaert et al, in J. Mol. Biol., 143:273–287 (1980).

Nucleotide Sequence of Trunip Yellow Nosaic Virus Coat Protein mRNA, by Guilley et al, in Cell, 15:113–122 (1978).

Isolation and Characterization of the Enzyme, by Butler and Chamberlin in J. Biol. Chem. 257(10):5772–5778 (1982).

Mapping of SP6 DNA and Selective In Vitro Transcription, by Lassavetis et al, in J. Biol. Chem. 257(10):5779–5788 (1982).

FIGURE 1

Viral Coat Protein mRNA Leader Sequences

Alfalfa Mosaic Virus m⁷GpppGUUUUUAUUUUAAUUUUCUUUCAAAUACUUCCAUC<u>AUG</u>

Black Beetle Virus m⁷GpppGUAAACAAUUCCAAGUUCCAAA<u>AUG</u>

Brome Mosaic Virus m⁷GpppGUAUUAAUA<u>AUG</u>

Satellite Tobacco Necrosis Virus

AGUAAAGACAGGAAACUUUACUGACUAAC<u>AUG</u>

Turnip Yellow Mosaic Virus m⁷GpppAAUAGCAAUCAGCCCCAAC<u>AUG</u>

PROCESS FOR ENHANCING TRANSLATIONAL EFFICIENCY OF EUKARYOTIC MRNA

BACKGROUND OF THE INVENTION

The Government has certain rights in this invention by virtue of NIH grant No. GM-34320.

This invention is in the general field of genetic engineering and in particular is a process for enhancing protein production.

Messenger RNA (mRNA) is translated into protein at different efficiencies, as shown by H. F. Lodish in *Ann. Rev. Biochem.*, 45: 39–72 (1976) and D. Kabat et al. in *J. Biol. Chem.*, 252: 2684–2690 (1977) using in virto systems. Competitive mRNA translation has also been reported for in vivo systems by B. Cordell et al. in *Cell*, 31: 531–542 (1982), Alton and Lodish in *Cell*, 12: 301–310 (1977), and G. E. Sonenshein in Biochem., 15: 5501–5506 (1976).

The data by Lodish, Kabat et al, Alton et al, in conjunction with data by B. K. Ray et al. in *Proc. Natl. Acad. Sci. USA*, 80: 663–667 (1983), indicate that the most significant site of regulation underlying translational discrimination is found at the level of initiation of protein synthesis. Protein synthesis is initiated with the recognition of a given mRNA molecule by ribosomal subunits and the initiator transfer RNA (tRNA), which leads to the formation of the first peptide bond linking two amino acids. There are numerous protein initiation factors involved in this process, such as the initiation factors described by R. Jagus et al. in *Prog. Nucleic Acid Research and Mol. Biol.*, 25: 127–185 (1981) and A. A. M. Thomas et al. in *FEBS Letters*, 128: 177–185 (1981).

Lodish showed preferential translation of mRNA using in vitro translation systems with saturating concentrations of mRNA. Those mRNA with the highest rate constant showed the maximum competitive activity. Differential mRNA translation is found with multicomponent plant virus mRNAs, in which the mRNAs encoding the viral coat proteins outcompete translation of both their companion viral RNAs and cellular mRNAs. This has been demonstrated by Herson et al. in *J. Biol. Chem.*, 254: 8245–8249 (1979), Ravelonandro et al. in *Nucl. Acids Res.*, 11: 2815–2826 (1983), Zagorski et al. in *Biochimie*, 65: 127–133 (1983), Godefroy-Colburn et al. in *Eur. J. Biochem.* (1985), Benicourt et al in *Biochem. Biophys. Res. Commun.*, 84: 831–839 (1978), and W. Zagorski in *Eur. J. Biochem.*, 86: 465–472 (1978). It has been proposed by Zagorski, Friesen et al. in *J. Virol.* 49: 116–124 (1984), Zagorski et al. and Pyne et al. in *Intervirology*, 11: 23–29 (1979) that the differential translation of the viral coat protein mRNAs may be a general feature in the replication strategy of RNA viruses which contain segmented, messenger-sense genomes.

As shown by these investigators as well as by Gehrke et al. in *Biochemistry*, 22: 5157–5164 (1983), the mechanism for the differential translation in these systems appears to center on both mRNA concentration and the initiation step of protein synthesis. The preferential synthesis of coat protein is not due to the accumulation of a virus-encoded protein which could selectively modify the host translational machinery. The data from viral and non-viral systems, including work by Grifo et al. in *J. Biol. Chem.*, 257: 5246–5252 (1982) and Iserentant et al. in *Gene* 9: 1–12 (1980), indicate instead that the level of competitive translation is determined by an inherent characteristic of the mRNA which enables the mRNA to compete for rate-controlling factors required for initiation of protein synthesis.

There have been several approaches to the problem of competitive translation, including mRNA primary sequence analysis and examination of the protein factors which could serve as "discriminatory factors". The scanning hypothesis expounded by M. Kozak in *Cell*, 22: 7–8 (1980) and modified in *Nucl. Acids Res.*, 9: 5233–5252 (1981) and *Cell*, 34: 971–978 (1983) states that 40S ribosomal subunits recognize the 5' end of mRNA sequences and then migrate down the sequence until the first AUG codon is encountered, at which point the 60S subunit joins the 40S subunit and the first peptide bond forms. There is some evidence which indicates that the "flanking" sequences surrounding the AUG codon may be important in regulating the efficiency of initiation of protein synthesis.

As taught by an article in *Nature*, 299: 221–226 (1982), Lomedico et al. created mutants with upstream in-frame AUG codons by connecting the 5' non-coding region of SV40 large T/small t antigen to the 5' noncoding region of the rat insulin II gene. These experiments indicated that ribosomes can recognize the most commonly used insulin initiation codon even if it is the seventh or tenth AUG codon from the 5' end. Taken together with the modified "scanning hypothesis", those data indicate that the nucleotide sequence and structure surrounding an initiation codon, as well as the position of the initiation codon relative to the 5' cap structure, are important in determining initiation efficiency.

Of the numerous potential "discriminatory features" inherent in mRNA which may be responsible for enhanced competitive translation, secondary structure is probably important. Kozak, Lomedico et al. and Ray et al. have disclosed data indicating that the 5' cap structure and the presence of an AUG codon at the beginning of the mRNA are insufficient to signal accurate translation initiation. Iserentant et al., Zabeau et al., Sonenshein et al., Kabat et al., Herson et al., and Sonenberg et al. have noted the likely importance of mRNA structure in modulating translational efficiency. Further, Berissi et al. in *Nature*, 234: 44–47 (1971); Sonenberg et al. in *Cell*, 27: 563–572 (1981) and Vermeer et al. in *Eur. J. Biochem.*, 40: 295–308 (1973) have shown that when denatured mRNA is used as a template with either eukaryotic or prokaryotic ribosomes, the requirement for some of the initiation factors is eliminated.

Despite all the data as to the importance of various factors on the rate at which a particular protein is produced, no one has yet succeeded in optimizing these factors to increase the rate of translation of a mRNA encoding the protein nor has one factor been isolated and adapted for use with a variety of genes, regardless of whether they are of plant or animal origin. Further, no one has provided such an isolated factor which can be used in vivo or in vitro with either the isolated gene for the protein or the cDNA encoding the protein.

It is therefore an object of the invention to utilize the features of mRNA sequence and structure which are required for high efficiency translation and protein production in engineered systems to produce mRNA sequences with enhanced mRNA translational efficiency.

It is a still further object of the invention to provide a method and means to increase the expression of a given protein without changing the structural, antigenic or biological features of the protein.

It is another object of the invention to construct suitable recombinant vectors which will transform plant and animal tissue to produce cells with increased production of a particular protein.

SUMMARY OF THE INVENTION

A process and means for increasing the production of protein translated from eukaryotic mRNA comprising transferring a regulatory nucleotide sequence from viral coat protein mRNA to the gene or cDNA sequence encoding the protein to be produced. The novel chimeric DNA sequences containing both the regulatory sequence and the sequence encoding the desired protein are generated using genetic engineering procedures to join the cloned gene encoding the protein of interest or a cDNA sequence encoding the protein of interest with synthetic double-stranded oligonucleotides which represent the viral regulatory sequence.

Examples of viral regulatory sequences useful in the present invention include the sequence preceding the initiator AUG codon and derived from the 5' terminus of coat protein mRNAs from alfalfa mosaic virus, brome mosaic virus, black beetle virus, turnip yellow mosaic virus, and satellite tobacco necrosis virus. These sequences encode a regulatory sequence or structure resulting in enhanced competitive activity and translatability.

DETAILED DESCRIPTION OF THE INVENTION

The present invention produces novel genetic sequences by joining regulatory sequences from viral coat protein mRNAs to any eukaryotic nucleotide sequence encoding a particular protein. To prepare a chimeric genetic sequence, the gene or cDNA is cloned in a suitable vector and propagated in either bacterial, plant or animal cells. Vector DNA is isolated using well-known procedures and then digested with one or more restriction enzymes to create a 5' terminal site for insertion of the viral coat protein messenger RNA sequence. Since the viral coat protein sequences are typically less than 100 nucleotides long, they are preferably made using synthetic oligonucleotide methodology. The regulatory sequence is covalently joined to the vector with DNA ligase, and the vector then used to transform or transfect prokaryotic or eukaryotic cells. Following the transcription of DNA into mRNA, the mRNA is translated with increased efficiency.

This method produces a chimeric mRNA molecule with enhanced translation into a protein, the final gene product. The novel chimeric sequences contain regulatory information in the form of non-translated nucleotide sequences derived from the 5' terminus of viral coat protein mRNAs. The viral sequence can significantly enhance translation of the chimeric messenger RNA molecules. However, since the virus-derived nucleotides are "non-coding", the protein complement of the native molecule is unchanged. Using this method, it is possible to increase expression of a given protein without changing its structural, antigenic, or biological features.

Figure 1:
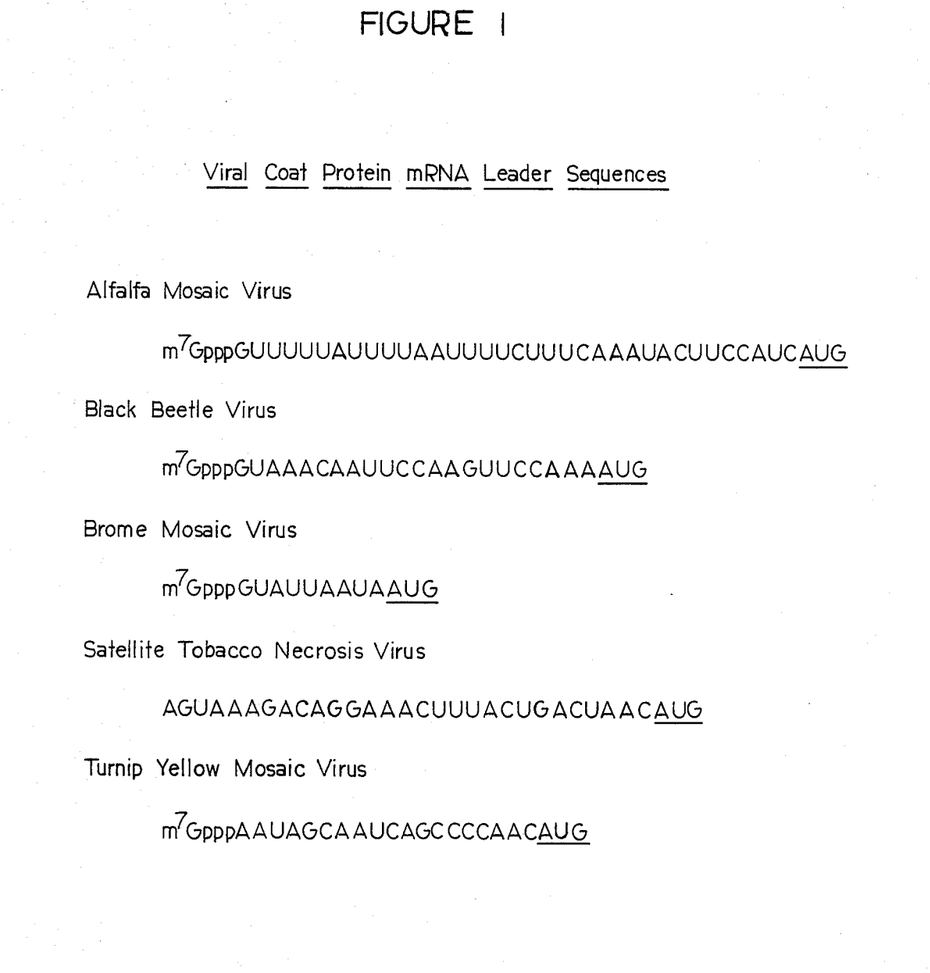
FIG. 1 are useful viral regulatory sequences.

The regulatory sequences which are useful in the present invention are identified as those sequences producing mRNA sequence and/or secondary structure in the 5' non-translated region which is recognized in a competitive manner and therefore has a modulating effect on the rate efficiency of translation. Examples of such sequences are shown in FIG. 1. The utility of the enhanced translational efficiency of viral coat protein mRNAs is related to the replication cycle of the virus. In vivo, viral coat protein is required in stoichiometric quantities to encapsidate newly replicated viral nucleic acid. This is in contrast to the quantitative requirement for production of the viral replicase enzyme which acts catalytically and therefore is needed in very small amounts. In general, coat protein mRNAs of viruses characterized by having multicomponent genomes are translated with a high level of efficiency.

The alfalfa mosaic virus nucleotide sequence is described by Brederode et al. in *Nucl. Acids Res.*, 8: 2213–2223 (1980); the black beetle virus nucleotide sequence is described by Dasgupta et al. in *Nucl. Acids Res.*, 12: 7215–7223 (1984); the brome mosaic virus nucleotide sequence is described by Dasgupta et al. in *Virology*, 104: 339–346 (1980); the satellite tobacco necrosis virus nucleotide sequence is described by Ysebaert et al. in *J. Mol. Biol.*, 143, 273–287 (1980); and the turnip yellow mosaic virus nucleotide sequence is described by Guilley and Briand in *Cell*, 15, 113–122 (1978). As is readily apparent, the majority of the sequences are characterized by being short, 40 nucleotides or less, and relatively poor in guanine. It is postulated that the sequences and/or structural features in the 5' non-translated region are recognized in a competitive manner by protein initiation factors which may serve to bind and destabilize mRNA secondary structure and facilitate increased translation efficiency.

The following examples are illustrative of the process and products of the invention, but are not to be construed as limiting.

Construction of a Plasmid containing a Chimeric Rabbit alpha-Globin cDNA with a 5' Leader Sequence Derived from Alfalfa Mosaic Virus RNA 4.

Rabbit alpha-globin mRNA was cloned using the method of Okayama and Berg in *Molec. Cell Biol.*, 2: 161-170 (1982) and subcloned into the PstI-BamHI sites of plasmid pSP64, obtained from Promega Biotec of Madison, Wis. Plasmid pSP64 contains the Salmonella phage SP6 promoter sequence described by Kassavetis et al. in *J. Biol. Chem.*, 257: 5779–5788 (1982) and Butler and Chamberlin in *J. Biol. Chem.*, 257: 5772–5778 (1982).

mRNA was synthesized in vitro using this vector and purified SP6 RNA polymerase, according to the method of Melton et al. in *Nucl. Acids Res.*, 12: 7035–7056 (1984). The rabbit alpha-globin sequence contains an NcoI site (recognition sequence C/CATGG) at position 35, near the initiator AUG codon (positions 37–39). The 5' non-translated leader sequence of alpha-globin is removed by digesting plasmid pSP64αU2 with HindIII, followed by incubation with T4 DNA polymerase and further digestion with NcoI. The two complementary strands of the ALMV RNA 4 leader sequence are synthesized by automated oligonucleotide synthesis according to the method of Beucage and Caruthers in *Tetrahedron Letters*, 22: 1859–1862 (1981) in a "gene machine" and annealed by heating in a salt solution followed by slow cooling according to the method of Maniatis et al. in *Molecular Cloning, A Laboratory Manual* (Cold Spring Harbor, NY, 1982). The double stranded oligonucleotide sequence is then joined to the linear vector DNA using DNA ligase. The resulting construct is a chimeric alpha-globin cDNA containing a 5' leader sequence derived from ALMV RNA 4.

Using well-known genetic engineering methods including the use of restriction endonucleases and DNA-DNA joining with DNA ligase, it is possible to insert one of the viral coat protein mRNA sequences at the 5' terminus of any cloned gene or cDNA encoding a particular protein. The viral sequences do not contain genetic information which is translated into protein. As a consequence, the protein complement of the chimeric sequence is unchanged as compared to the native molecule.

Figure 2:
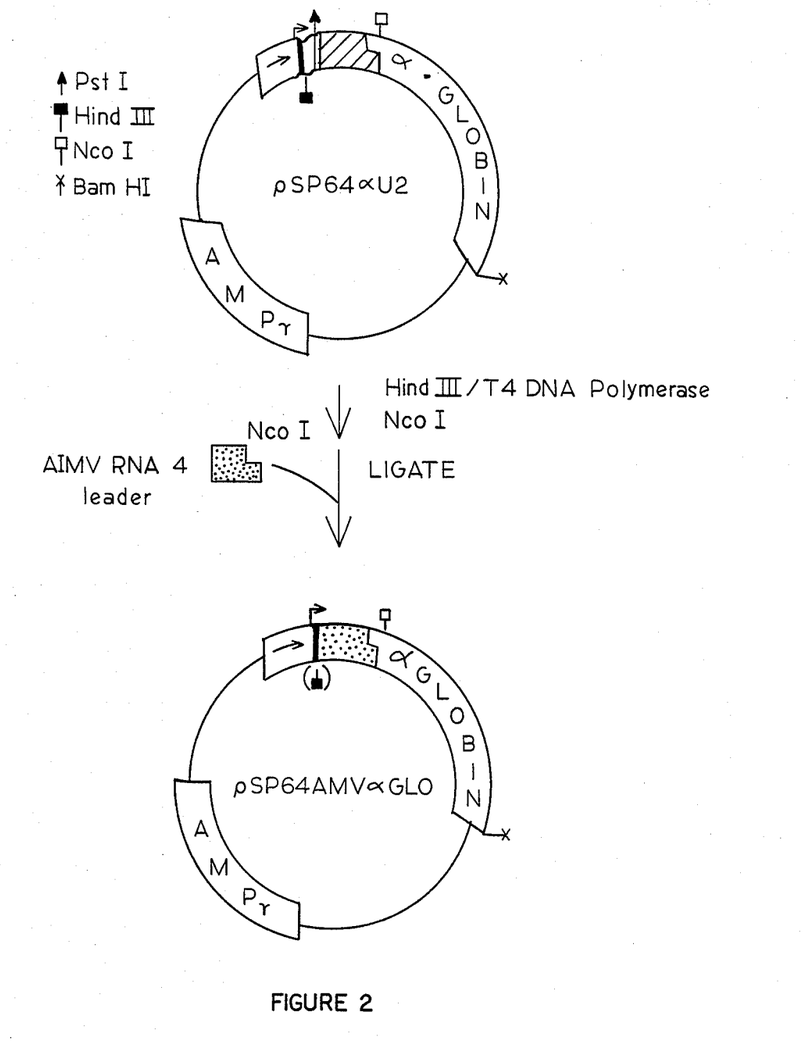
FIG. 2 is a schematic illustrating the replacement of the untranslated nucleotide leader sequence preceding the alpha globin cDNA coding sequence in plasmid pSP64αU2 with the untranslated leader sequence derived from alfalfa mosaic virus RNA 4 to generate pSP64AMVαGlo.

Example Showing Increased mRNA Translational Efficiency Resulting From Insertion of Coat Protein Regulatory Nucleotide Sequence Rabbit alpha-globin was cloned using the Okayama-Berg vector, described by H. Okayama and P. Berg in "High Efficiency cloning of full-length cDNA" in *Mol. Cell. Biol.*, 2: 1161 (1982), and the cloned cDNA subcloned into the PstI-BamHI sites of pSP64, as shown in FIG. 2.

Figure 3:
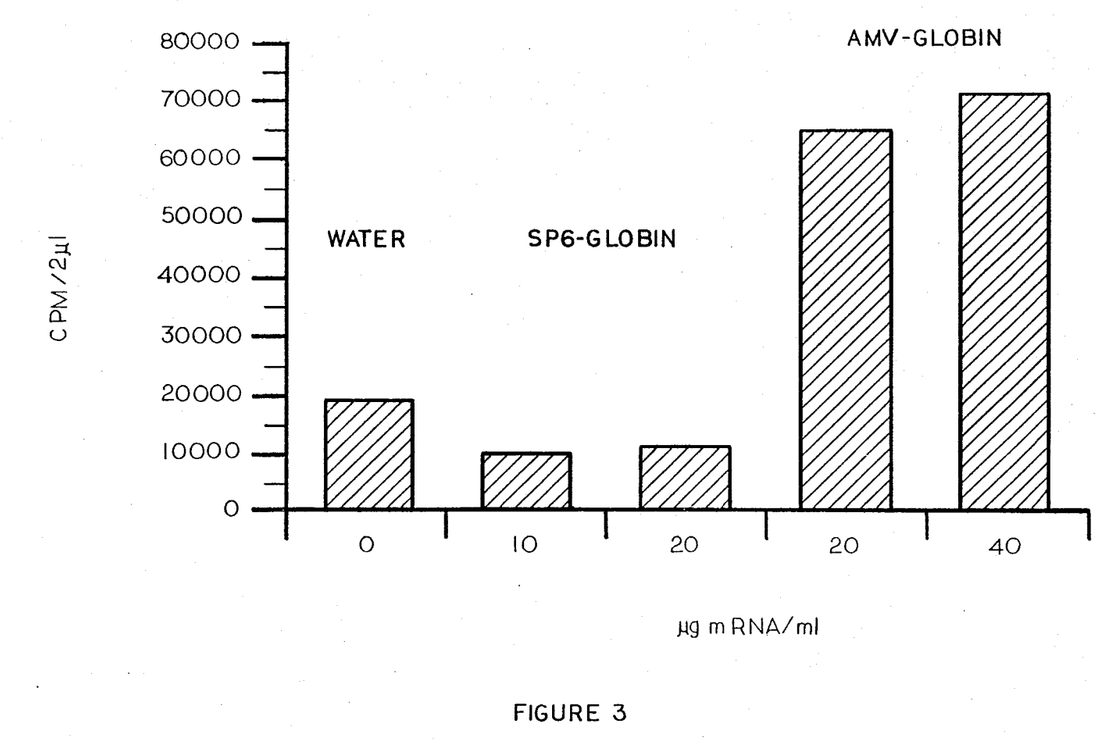
FIG. 3 is a comparison of total protein (CPM) produced during in vitro protein synthesis in a reticulocyte lysate in the absence of added mRNA ("water") and in the presence of the alpha globin coding sequence preceded by either SP64, Okayama-Berg, and native untranslated sequence ("SP6 Globin"), or preceded by the untranslated leader sequence derived from a small number of SP64 nucleotides joined to the A1MV 4 leader ("AMV-Globin").

The alpha-globin mRNA transcribed from this vector using SP6 polymerase contains approximately 35 nucleotides of 5' sequence derived either from the SP6 vector or Okayama-Berg vector and preceding the true 5' end of the mRNA. This mRNA does not translate in the reticulyte or wheat germ translation system. (Commercial reticulyte lysate or extract of wheat germ translation systems can be obtained from New England Nuclear, Boston, MA, or Bethesda Research Labs.) In fact, the SP6-alpha-globin apparently inhibits endogenous incorporation of $^{35}$S-methionine, as shown in FIG. 3. Computerized dot matrix analysis of the nucleotide sequence reveals that the SP6-alpha-globin clone has the potential for forming the structure shown in FIG. 4. In the proposed structure, the initiator AUG condon, nucleotide positions 72–74, is preceded by two stable hairpin structures. The stem-loop structures involve both the 5' non-translated leader region and sequence located immediately downstream from the initiation AUG and may present a significant block to initiation of translation.

Figure 4:
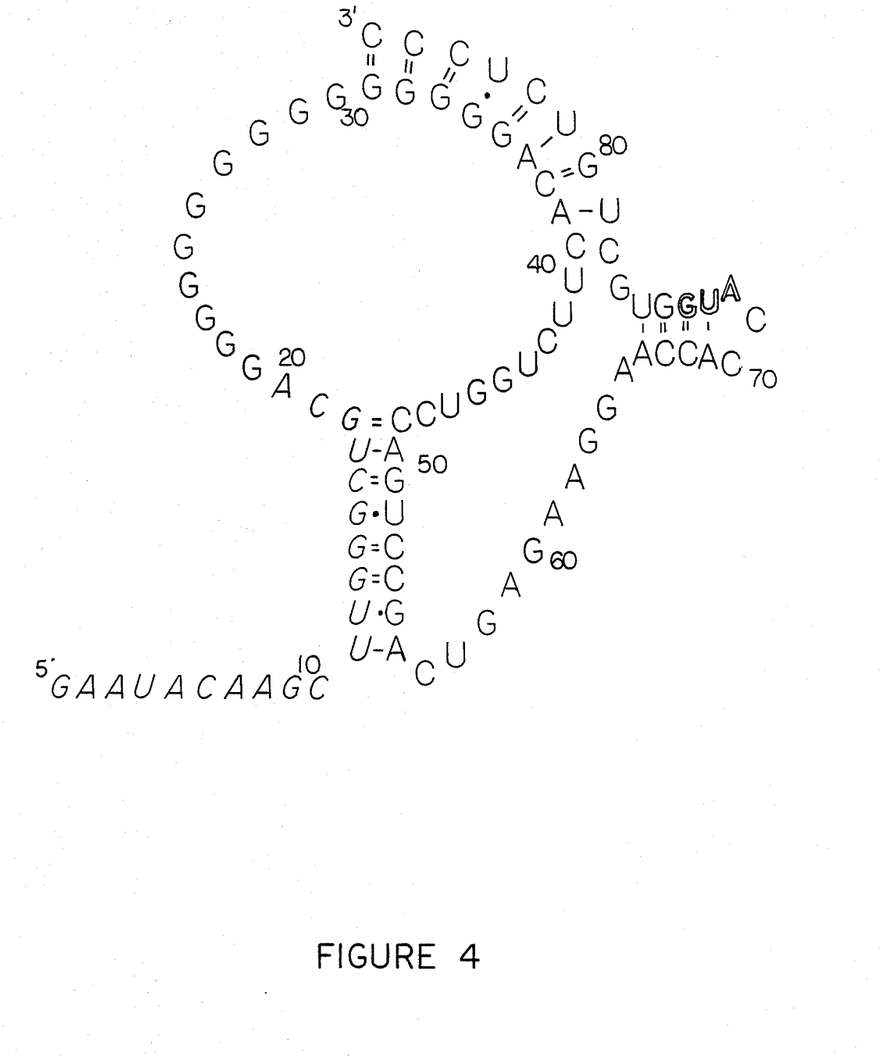
FIG. 4 is a secondary structure model of the 5' terminus of SP6-globin mRNA as determined by computerized dot matrix analysis.
Figure 5:
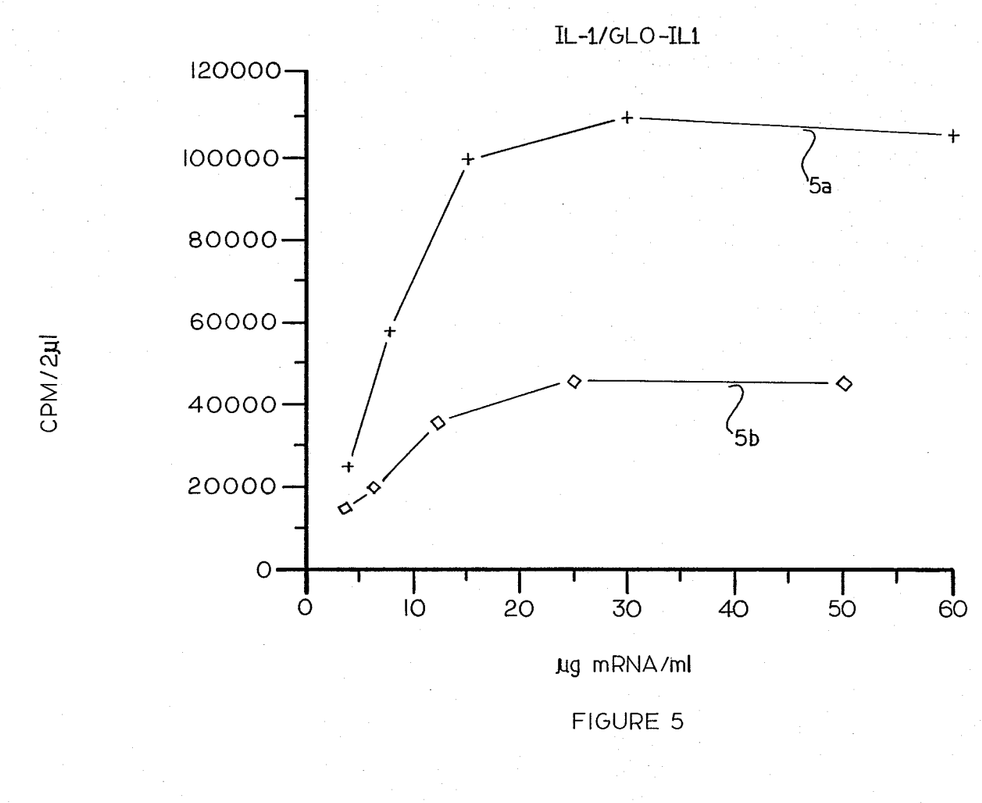
FIG. 5 is a comparison of the total protein (CPM) produced by in vitro translation of human interleukin-1 mRNA under the influence of untranslated leader sequence derived from vectors SP64 and Okayama-Berg combined with the natural leader, or as influenced by sequences derived from vectors SP64 and Okayama-Berg combined with natural sequences from rabbit alpha globin mRNA.

It is unlikely that the 5' oligo G sequence alone decreases the rate of translation. The 5' oligo G region shown in FIG. 4 is derived from the Okayama-Berg cloning vector. As shown in FIG. 5, addition of an SP6-IL1 mRNA encoding human interleukin-1, produced from IL1 cDNA subcloned into pSP64 at the Pst-Bam sites and having the same 5' terminal sequence of 35 nucleotides, to an in vitro translation system stimulates protein synthesis to a level approximately 5-fold over background. Comparison of the translation rates for the SP6-IL1 mRNA and the SP6-alpha-globin mRNA indicates that the 5' oligo G sequence alone is not responsible for blocking translation but that structural changes due to pairing between alpha-globin sequences and vector sequences in the SP6-alpha-globin mRNA inhibits translation.

The rate of translation of the SP6-alpha-globin mRNA is greatly enhanced by deleting the 5' nontranslated leader sequence between nucleotides 12 and 67 and inserting an oligonucleotide representing the 5' nontranslated leader of alfalfa mosaic virus RNA 4, as shown in FIG. 3.

Replacement of the leader sequence with another nucleotide sequence is not sufficient in itself to increase the rate of translation. Translational efficiency can be decreased by replacing the 5' nontranslated leader, as shown by FIG. 5. FIG. 5 compares the translation of SP64 IL1 mRNA (line 5a) and SP64-IL1 under the influence of the alpha-globin leader, nucleotides 1–68 shown in FIG. 4 (line 5b). The comparison was made by subcloning an NcoI partial/BamHI fragment of the IL1 cDNA into the NcoI-BamHI site of SP6-globin. The effect of the globin 5' nontranslated leader on the translation of the IL1 coding sequence is to decrease the translational efficiency nearly 3-fold.

The chimeric viral regulatory sequence-protein encoding mRNA can be introduced into procaryotic plant or animal cells by transduction, transformation or electroporation. With the first method, the chimeric mRNA is introduced into the cells using a virus. In the second method, membrane disruption agents such as calcium chloride are used. One example of such a method is described by Maniatis et al. in "Molecular Cloning", p. 248–255 (Cold Spring Harbor Laboratory 1982). In electroporation, an electric field is used to reversibly disrupt cellular membrane structure to allow passage of nucleic acids. The introduced genetic material is replicated within the cells, transcribed into mRNA, and then translated into protein.

Although this invention has been described with reference to specific embodiments, it is understood that modifications and variations of the disclosed methods and products may occur to those skilled in the art. It is intended that all such modifications and variations be included within the scope of the appended claims.

I claim:

1. A process for increasing protein production from a eukaryotic nucleotide sequence comprising
   (a) selecting a guanine-deficient 5' non-translated nucleotide sequence from a eukaryotic viral protein gene,
   (b) selecting a nucleotide sequence encoding a protein to be expressed, wherein the selected sequence is non-cognate to the protein sequence from which the 5' non-translated sequence was isolated and the 5' non-translated sequence does not form stable structure with itself or the protein encoding sequence due to the relatively low incidence of guanosine-cytosine base pair formation within the 5' non-translated sequence and between the 5' non-translated sequence and the protein encoding sequence,
(c) joining said non-translated nucleotide sequence to the 5' terminus of the nucleotide sequence encoding the protein to be produced to yield a chimeric protein-encoding nucleotide sequence,
(d) expressing the protein, and
(e) selecting the chimeric sequences wherein the chimeric mRNA is translated more efficiently than the protein encoding sequence in combination with its cognate 5' non-translated leader sequence, wherein the rate of translation is measured as the rate of initiation of protein synthesis and the increase in translational efficiency is not dependent on the presence of a Shine-Delgarno sequence in the 5' non-translated sequence.

2. The process of claim 1 wherein said non-translated sequence is selected from the group consisting of:
m$^7$GpppGUUUUUAUUUUAAUUUUCUUUCAAAUACUUCCAU;
m$^7$GpppGUAAACAAUUCCAAGUUCCAAA;
m$^7$GpppGUAUUAAUA;
AGUAAAGACAGGAAACUUUACUGACUAA; and
m$^7$GpppAAUAGCAAUCAGCCCCAAC.

3. The process of claim 1 further comprising synthesizing said non-translated nucleotide sequence as a double-strand oligonucleotide sequence of about 125 nucleotides or less.

4. The process of claim 1 further comprising combining a non-translated sequence from said selected chimeric protein-encoding sequences with a sequence encoding a third protein and expressing the third encoded protein.

5. The process of claim 1 wherein said protein encoding sequence is a cDNA sequence.

6. The process of claim 1 wherein said protein-encoding sequence is the chromosomal DNA containing nucleotide sequences encoding the protein to be produced.

7. The process of claim 6 wherein said regulatory nucleotide sequence is joined to the 5' terminus of the protein-encoding sequence by
isolating the DNA sequences encoding the protein to be produced;
digesting said isolated DNA with restriction endonucleases to create a 5' terminal site; and
covalently joining said non-translated nucleotide sequence to said digested, isolated DNA to form a chimeric protein-encoding sequence.

8. The process of claim 1 further comprising introducing said chimeric sequence into cells selected from the group consisting of eucaryotic and procaryotic cells.

9. The process of claim 8 wherein said chimeric sequence is introduced into plant cells by electroporation.

10. The process of claim 8 wherein said chimeric sequence is introduced into the cells by transformation.

11. The process of claim 8 wherein said chimeric sequence is introduced into the cells by transduction.

12. A chimeric protein-encoding nucleotide sequence with enhanced competitive activity and rate of translation comprising:
a nucleotide sequence encoding a first protein and
a non-cognate guanine-deficient viral 5' non-translated nucleotide sequence,
wherein the 5' non-translated sequence does not form stable structure with itself or the protein encoding sequence due to the relatively low incidence of guanosine-cytosine base pair formation within the 5' non-translated sequence and between the 5' non-translated sequence and the protein encoding sequence and the combination of said non-translated sequence and said first protein messenger RNA is translated with greater competitive activity and translational efficiency than the first protein messenger RNA in combination with its cognate 5' non-translated leader sequence, the rate of translation being measured as the rate of initiation of protein synthesis, wherein the increase in translational efficiency is not dependent on the presence of a Shine-Delgarno sequence in the 5' non-translated sequence.

13. The chimeric protein-encoding nucleotide sequence of claim 12 wherein said non-translated sequence is selected from the group consisting of:
m$^7$GpppGUUUUUAUUUUAAUUUUCUUUCAAAUACUUCCAUCAUG;
m$^7$GpppGUAAACAAUUCCAAGUUCCAAAAUG;
m$^7$GpppGUAUUAAUAAUG;
AGUAAAGACAGGAAACUUUACUGACUAACAUG; and
m$^7$GpppAAUAGCAAUCAGCCCCAACAUG.

14. The chimeric protein-encoding nucleotide sequence of claim 12 wherein said protein encoding nucleotide sequence is cDNA.

15. The chimeric protein encoding sequence of claim 12 wherein said regulatory sequence is a synthetic double-stranded oligonucleotide sequence.

16. The chimeric protein encoding sequence of claim 12 wherein said protein encoding nucleotide sequence is chromosomal DNA.

17. The chimeric protein encoding sequence of claim 12 wherein said chimeric sequence has a higher relative affinity for a limiting component of the translation system than the protein encoding sequence in combination with its cognate 5' non-translated sequence.

18. The chimeric protein encoding sequence of claim 12 wherein said chimeric sequence has a higher relative affinity for a limiting component of the translation system than the protein encoding sequence in combination with its cognate 5' non-translated sequence.

19. The chimeric protein encoding sequence of claim 12 wherein said chimeric sequence has a diminished requirement for a limiting component of the translation system than the protein encoding sequence in combination with its cognate 5' non-translated sequence.

* * * * *

UNITED STATES PATENT AND TRADEMARK OFFICE
CERTIFICATE OF CORRECTION

PATENT NO. : 4,820,639
DATED : April 11, 1989
INVENTOR(S) : Lee Gehrke

It is certified that error appears in the above-identified patent and that said Letters Patent is hereby corrected as shown below:

Title page, Abstract, line 8, change "sequence" to --sequences--.
      "19 Claims, 5 Drawing Sheets" should read
      --18 Claims, 5 Drawing Sheets--.
Column 1, line 14, change "in virto" to --in vitro--.
Column 8, claim 18 duplicates claim 17 and should be deleted.
Column 8, renumber claim 19 as claim 18.

Signed and Sealed this

Twenty-sixth Day of December, 1989

Attest:

JEFFREY M. SAMUELS

Attesting Officer     Acting Commissioner of Patents and Trademarks